United States Patent [19]

Alexeev et al.

[11] Patent Number: 5,409,011
[45] Date of Patent: Apr. 25, 1995

[54] BIOENERGY ASSESSING METHOD AND SYSTEM FOR DIAGNOSING AND PROVIDING THERAPY

[76] Inventors: Vassili Alexeev, P.O. Box #240, Nyack, N.Y. 10960; Vitaly Popov, 67 Perekopskaia Divizia, Apt. 132, Odessa, 270062, Ukraine

[21] Appl. No.: 88,269

[22] Filed: Jul. 7, 1993

[51] Int. Cl.⁶ .............................................. A61B 5/04
[52] U.S. Cl. ................................... 128/734; 128/733; 128/741
[58] Field of Search ................... 128/734.5, 732.3, 741, 128/731

[56] References Cited

U.S. PATENT DOCUMENTS

| | | |
|---|---|---|
| 3,784,908 | 1/1974 | Anderson ....................... 128/734 X |
| 3,894,532 | 7/1975 | Morey . |
| 3,905,355 | 9/1975 | Brudny . |
| 3,942,516 | 3/1976 | Glynn et al. . |
| 3,978,847 | 9/1976 | Fehmi et al. . |
| 4,031,883 | 6/1977 | Fehmi et al. . |
| 4,557,271 | 12/1985 | Stoller et al. ....................... 128/734 |
| 4,651,280 | 3/1987 | Chang et al. ................... 128/734 X |
| 5,144,554 | 9/1992 | Zhang et al. . |
| 5,271,413 | 12/1993 | Dalamagas et al. ................ 128/734 |

Primary Examiner—Angela D. Sykes
Attorney, Agent, or Firm—Ostrolenk, Faber, Gerb & Soffen

[57] ABSTRACT

A system and method are provided for diagnosing, therapy, and/or prevention of a plurality of diseases. The method is based on an assessment of data, reflecting the level of inner bioenergy produced by a human body. The system performs a multichannel data acquisition, processes the data, generates a diagnosis, and provides a prescription for the therapy. The system exists in several embodiments and generally includes a set of diagnostic and therapy electrodes, an input demultiplexer, analog-to-digital converter, output demultiplexer, a computer, power and control units, and a portable data acquisition unit.

50 Claims, 10 Drawing Sheets

SPLEEN-PANCREAS MERIDIAN

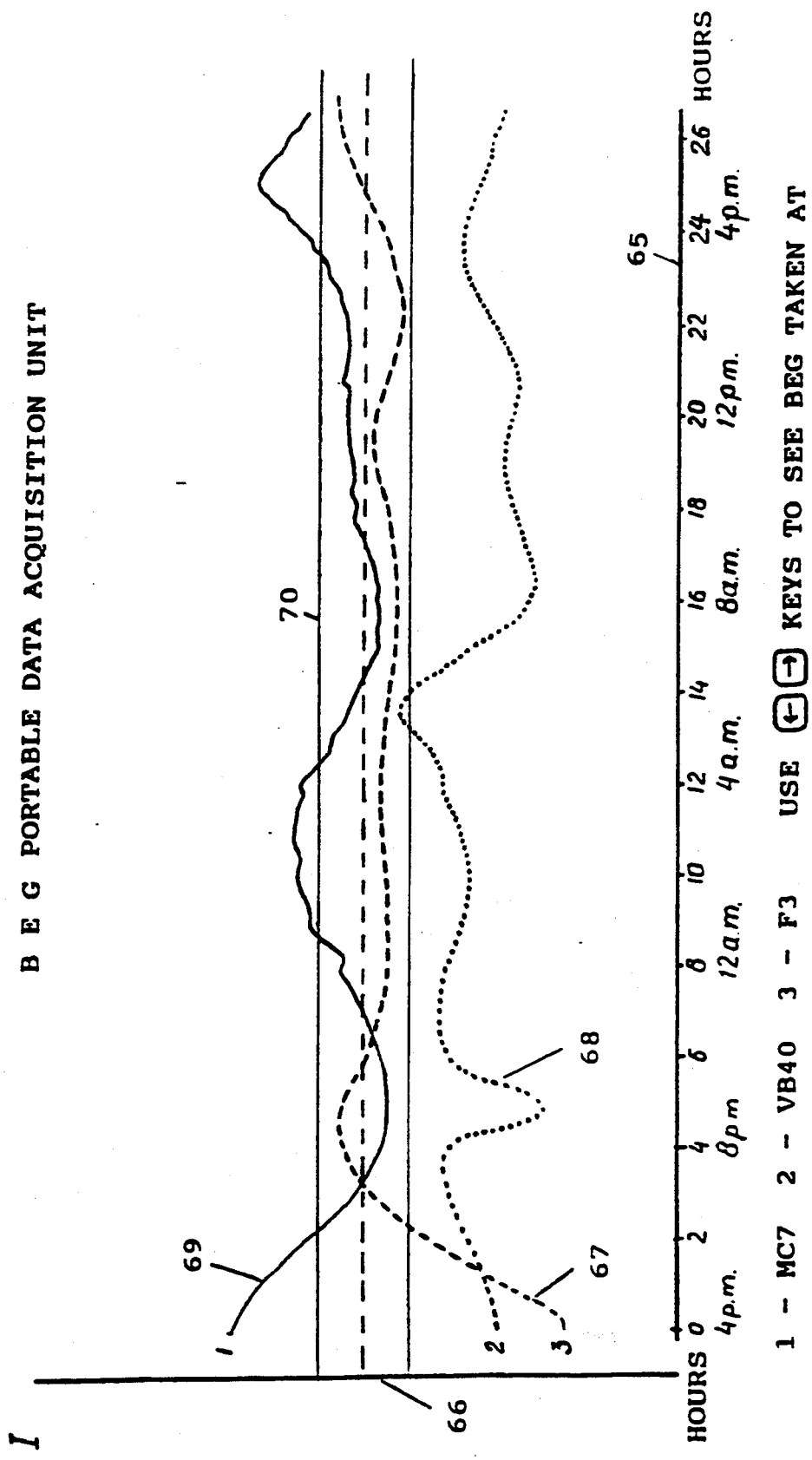

BIOENERGY ASSESSING METHOD AND SYSTEM FOR DIAGNOSING AND PROVIDING THERAPY

BACKGROUND OF THE INVENTION

The present invention relates to diagnostic and therapeutic methods and apparatus, particularly to those which use bioelectrical characteristics of a human body as primary data. Heretofore, medical instruments and methods employed have been processing a variety of electrical signals due to bioelectrical and biochemical activities of a human body, such as brain waves (EEG), skin potentials, impulses related to general muscle activity (EMG), or specifically, heart muscle activity (EKG), and a variety of other potentials from other areas of the human body. The relative values of the potentials (voltages) are very small—for constant or slowly changing potentials, the value is about tens microvolts and for fast changing ones (impulses) the amplitude is less than 250 microvolts. The widest applications have been achieved by those devices which have processed changing potentials—impulses, or electrical waves. Some of the instruments and methods measure passive characteristics of the body, such as an impedance (skin resistance or resistance between two given points). In the last case, to obtain data (either current or resistance), a source of external voltage must be applied, but this also affects inner body structures in unpredictable ways, so that the informative level of the data is low.

SUMMARY OF THE INVENTION

The present invention employs the ability of a human body to produce energy on a comparatively large scale without the influence of any external sources of energy.

Although the present invention relates to a wide field of traditional physiotherapeutic methods and instruments, it also relates to some elements of alternative medicine. The invention relates, e.g. to the concept of "inner bioenergy".

Energy is an important theme in alternative healing, and so far it has not had any real equivalent in conventional medicine. In the present invention, the energy is real and has simple biochemical and physical substance and explanation.

The definition of any kind of energy is the ability to perform some work. The ability of the human body to produce an electrical current under specific conditions, i.e. to perform work on moving charged particles—ions, electrons—is used in the device of the invention. This condition occurs when two different electrodes made of different materials are applied to a part of the human body. The well-known effect is to produce a difference in electrical potentials. But when an external short circuit is made the current in the circuit is determined only by the capacity of the "live battery" made of electrodes and the body, which in turn is a complex biochemical substance consisting of the combinations of cardiovascular and neurophysiological systems, skeletal structure and muscles, tissues and organs. Thus, the current level depends only on the inner complex bioconductivity and the sum of potentials and complex charged units; for example, ions in blood vessels, or cells, each of which in turn might be considered as a tiny power station. Therefore, the value of the generated current represents the condition of inner structures of the body between the points of electrode application. This value is comparatively high, up to 250 microamperes. Such a high level of energetic ability of the body allows excluding unwanted interference and accidental readings of extraneous signals.

The points of electrode application are taken from the practice of the ancient Chinese art of acupuncture. A large database regarding finding the relationship between the classical acupuncture points (acupoints) and inner organs and life systems of a human body has been collected. The whole chart of more than 600 points has been organized into the Yin-Yang System of 14 basic meridians (12 twin meridians—left side, right side, and 2 nonpair meridians). The present invention may employ the twin meridians (French system of denominations): Stomach (E), Small intestine (IG), Large intestine (GI), Bladder (B), Gall bladder (G), Triple warmer (TR), Heart (C), Lungs (P), Liver (F), Spleen-Pancreas (RP), Kidney (R), Circulation-sex (MC). All meridians have specific points, which are called representative. The state of these points reflects the condition of the related meridians and correlated inner organs and life functions of a human body. These points are located at extremities and used in the present invention as points of application of the meridian electrodes—one electrode for each meridian ("input" points). Whereas all meridians end in the body, one common point for all electrodes is to be located at the stomach area ("output" point). The common electrode and meridian electrodes are made of different materials.

Although the French System of meridian denominations is used in the described embodiment of the invention, other systems of meridian description can also be used, as would be known to those of skill in the art.

It is possible that for different methods of the applications of the present invention the input points as well as output points could be different.

Before entering into a detailed consideration of the objects and structural aspects of the invention, the following definitions should be made.

A system comprised of two applied electrodes, a meridian and a common electrode, and an inner human body's substance between them, constitutes a source of bioelectrical energy.

An inner human body's substance between input and output points constitutes a channel of the energy flow (channel). The values of electrical currents generated by the sources of bioelectrical energy constitute primary data.

A chart of relatively placed scales of possible values of electrical currents generated by a human body, corresponding to each meridian is a biodiagram. The relatively placed scales, as described later, corresponding to each meridian, do not necessarily have the same scaling. The scaling for each scale can be different so that a value on one scale corresponding to a meridian may lie opposite a different value on the adjacent scale for another meridian. This will be explained in more detail later. The scaling for each meridian typically is obtained from experience in obtaining measurements corresponding to each meridian from organisms known to be healthy.

A graph, reflecting the primary data plotted on the biodiagram, is referred to herein as a Bio-Energy-Gram (BEG). Treatment by means of relocation of the human body's inner energy without any external source of energy is referred to as biotherapy.

An object of the present invention is to provide a method and a system for assessing the data representing the level of inner bioenergy produced by a human body and of the balance of that energy, and, relying on the results of the assessment, to generate a diagnosis and a prescription for biotherapy.

A principal functional object of the invention is to make a human body generate energy, to collect through the multichannel system of measurement the data, representing the level of the energy of multiple sources on the body, and to put the data through the process of assessment and displaying in the form of a Bio-Energy-Gram.

Insofar as a plurality of physiological functions of a human body act in reciprocity at any given moment, it is another object of the invention to perform the data acquisition instantaneously to obtain a "snapshot" of the balance of inner energy.

Considering that the primary data are generated by the human body without any external sources of energy and are different by their nature from the data used in heretofore existing devices, it is among the principal objects of the present invention to provide alternative means for diagnosing. Therefore, the obtained diagnosis can either confirm an already existing one or discover disease which can not be diagnosed by conventional examinations or means.

In the perspective of diagnosing, another object of the invention is to guide an attending physician in obscure situations when a patient's complaints are not determined or are controversial and it is not clear which type of examination to choose. Therefore, with the help of the invention, the search can be narrowed down and, in some cases of escalating diseases, precious time will be saved and/or expensive, dangerous or unnecessary tests will be avoided.

Experiments show that the bioelectrical signals used in the present invention highly correspond to any minor changes in the body's condition, so it causes noticeable change in the resulting BEG. Therefore, another object of the invention lies in the possibility of preventing any disease to which the body may be predisposed by the change in the human body. The manner of prevention lies in two dimensions. The first one contemplates an alert physician's attention to a number of possible abnormalities in inner organs or life systems. The organs or systems are appointed by the interrelations between them and location of the corresponding acupuncture meridians. The second dimension is to provide the physician with a prescription on how to restore the balance of inner energy, thus to eliminate the risk of any possible disease.

Another object of the invention is providing a therapy in which inner energy is relocated in the manner pointed out in the prescription. Following the prescription can provide temporary relief, or faster healing, or complete recovery.

A further object of the invention is to provide the bioenergetic therapy without the need for medication, thus to avoid the side effects of pharmacotherapy or to provide an alternative treatment when it is not possible or it is dangerous to apply conventional medication.

Another object of the present invention lies in the possibility of creating a personal bioenergetic data bank for each patient as a personal template of bioenergy balance for periodic checkups. Both patients who are ill or have been ill and are recovering as well as those who are healthy and not under a doctor's care can benefit from this. Any steady significant change in the BEG should alert the physician and make him decide about further examinations. This feature of the invention can be described as a preventive function at the very early stage of a disease or of a predisposed condition and may allow preventive therapies to be used even if there is no other evidence that has appeared for concern.

Although the whole BEG is to be taken in a physician's office, another object of the invention is to provide the physician with the possibility of investigating some revealed abnormalities in the BEG by using a portable data acquisition unit, which can be programmed for a certain period of time and carried with the patient for that period. This allows collection of data from suspected points and, after displaying the data, the determination of whether the changes are steady and should be taken into consideration or they are due to any temporary effects or factors, such as, for example, food, weather, and stress.

Considering the high sensitivity of the primary data, another object of the invention is to provide a physician with a new tool for developing new methods of diagnosing, treatment, and/or preventive therapy in any field of medicine. Some of these methods have been tested such as for chronic fatigue syndrome and dieting. The invention has also been tested and experiments performed using it in the treatment of children suffering from the effects of the Chernobyl nuclear plant disaster.

Yet another object of the present invention lies in combining it with conventional means during diagnosing or treatment, since a BEG can be evidence of either positive or negative changes during any kind of treatment or testing (including biotherapy).

It is among other possible applications of the system that it can be used to control daily, monthly, and/or seasonal cycles of inner energy activities known as biorhythms. This feature allows prevention of possible disorder or a warning to restrict some working activities, e.g., of those whose activities include frequent stress and/or burdens of high responsibility.

The above and other objects of the present invention are achieved by a method for assessing the physical condition of an organism, comprising: applying a plurality of electrode pairs to the organism, at least one of the electrodes in each electrode pair being polarizable and an electrode in each pair being of a different material than the other electrode in the pair, an electrical current thereby being generated between the electrodes in each electrode pair; determining the electrical current between the electrodes in each pair so as to obtain a plurality of current measurements; comparing the determined electrical current for each electrode pair with a respective value for each electrode pair corresponding to an organism known to be healthy; determining if the electrical current for each electrode pair is within an acceptable range of the respective value for each electrode pair corresponding to the organism known to be healthy and assessing the physical condition of the organism based upon the relationship of the electrical currents to the acceptable range.

Preferably, the step of applying comprises applying a plurality of site-specific electrodes and one common electrode to the organism, thereby to provide a plurality of current sources, each current source between a respective site-specific electrode and the common electrode defining an electrode pair; the first step of determining comprises determining the electrical current generated between each of the plurality of site-specific electrodes and the common electrode; the step of comparing comprises comparing the electrical current for each electrode pair with a respective value for each electrode pair corresponding to an organism known to be healthy; the second step of determining comprises determining if the electrical current for each electrode pair is within an acceptable range of the respective value for each electrode pair corresponding to the organism known to be healthy; and the step of assessing comprises assessing the physical condition of the organism based upon the relationship of the electrical currents to the acceptable range for each of the electrode pairs.

In a particular embodiment, the step of determining the electrical currents comprises measuring an electrical current value by determining a voltage, e.g., across a resistance.

The objects of the invention are furthermore achieved by an apparatus for assessing the physical condition of an organism, comprising: means for receiving inputs from a plurality of electrode pairs appliable to the organism, at least one of the electrodes in each electrode pair being polarizable and an electrode in each electrode pair being of a different material than the other electrode in the pair, an electrical current thereby being generated between the electrodes in each electrode pair when applied to the organism; first means for determining the electrical current between the two electrodes in each pair so as to obtain a plurality of current measurements; means for comparing the determined electrical current for each electrode pair with a respective value for each electrode pair corresponding to an organism known to be healthy; second means for determining if said electrical current for each electrode pair is within an acceptable range of the respective value for each electrode pair corresponding to the organism known to be healthy; and means for assessing the physical condition of the organism based upon the relationship of the electrical currents to the acceptable range.

Preferably, the means for receiving comprises means for receiving inputs from a plurality of site-specific electrodes and one common electrode, thereby to provide a plurality of current sources, each current source between a respective site-specific electrode and the common electrode defining an electrode pair; the first means comprises means for determining the electrical current generated between each of the plurality of site-specific electrodes and the common electrode; the means for comparing comprises means for comparing the electrical current for each electrode pair with a respective value for each electrode pair corresponding to an organism known to be healthy; the second means comprises means for determining if the electrical current for each electrode pair is within an acceptable range of the respective value for each electrode pair corresponding to the organism known to be healthy; and the means for assessing comprises means for assessing the physical condition of the organism based upon the relationship of the electrical currents to the acceptable range for each of the electrode pairs.

In a particular embodiment, the first means comprises means for determining an electrical current value by measuring a voltage, e.g., across a resistance.

These objects as well as other objects and advantages of the invention will more fully appear in the progress of the following disclosure and will be pointed out in the appended claims.

BRIEF DESCRIPTION OF THE DRAWINGS

With the foregoing discussion in mind, reference may now be had to the accompanying drawings, in which:

FIG. 5 is a portable data acquisition unit (PDAU) data display;

In the drawings, like parts will be indicated by like reference numerals.

DESCRIPTION OF THE METHOD AND PREFERRED EMBODIMENT OF THE SYSTEM

Figure 1:
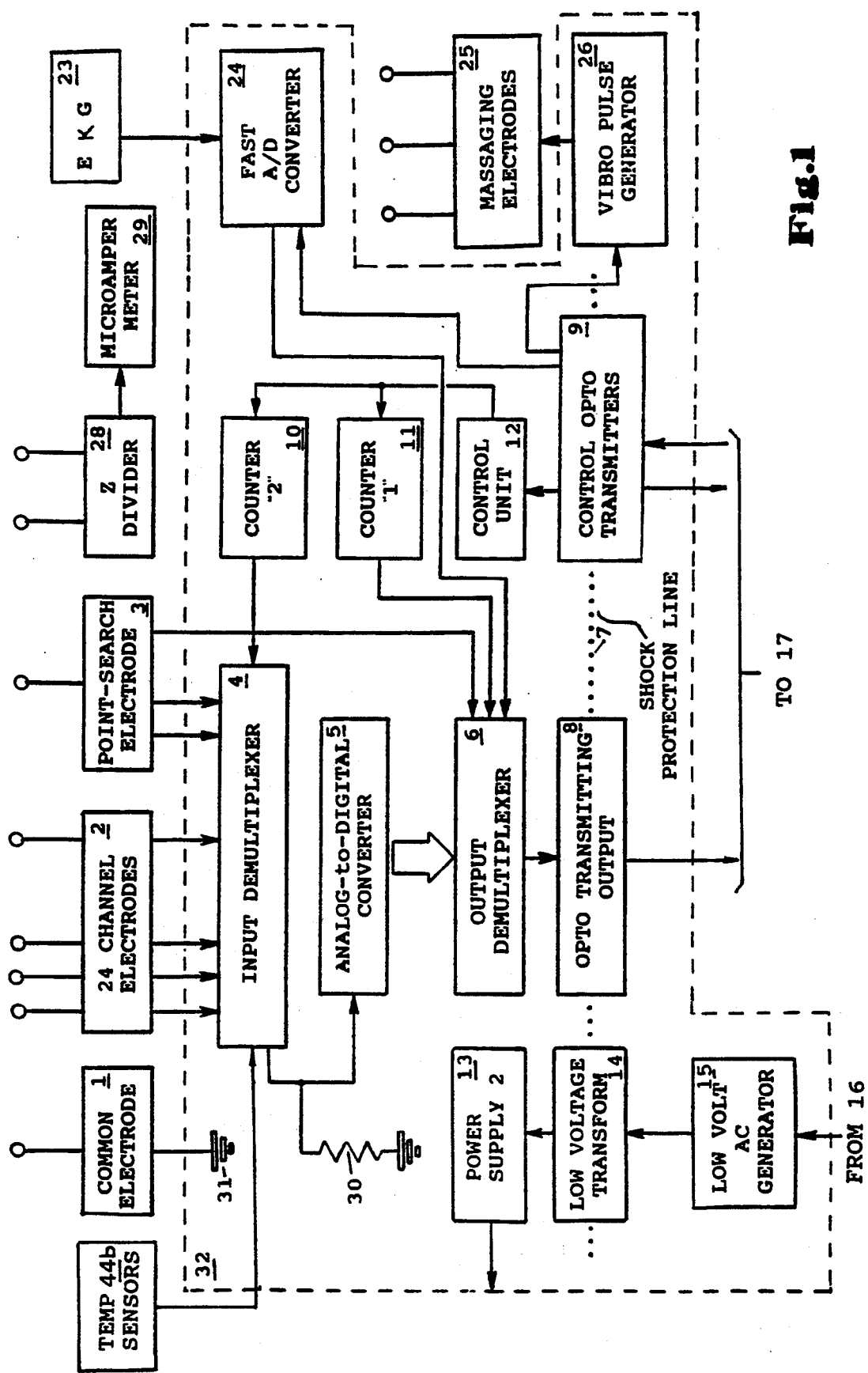
FIG. 1 is a schematic block diagram of the system according to the invention.
Figure 1A:
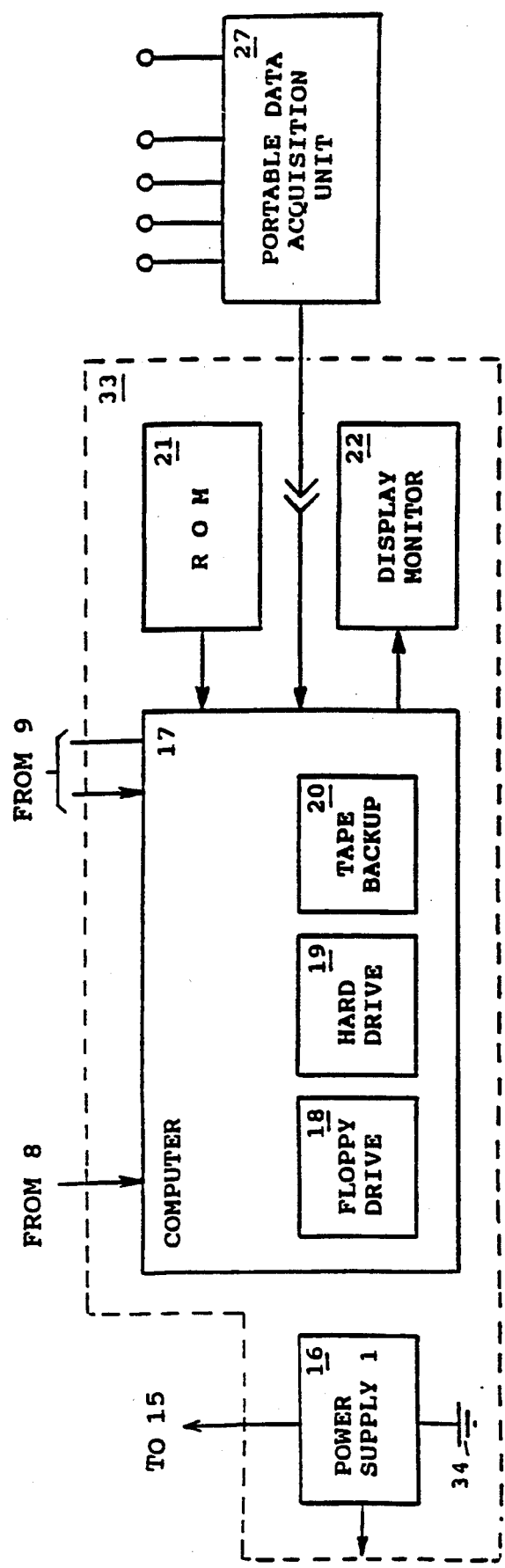

In accordance with the objects of the present invention, the system is to be able to accomplish the following basic functions: data generation, data acquisition, data processing, display of the results (BEG), processing of the results (generating prescriptions, files operations), and performing specific application programs.

1. Data generation

The source of electrical energy made of the human body and electrodes is similar to a battery made of different polarizable electrodes placed into electrochemical solution. According to the natural law of electro-chemical separation of charges, in the case of a battery, opposite electrical potentials are created on the electrodes, thus an electromotive force is generated, which can create an electrical current in an external conducting circuit. If the electrical conductivity of the external circuit is infinite, the level of the produced current depends only on the nature and condition of the electrodes and solution/medium between them.

A primary mechanism of producing energy by the human body is similar to the one just described, but experiments show that the whole process can not be narrowed down to that simple explanation. The biochemical substance of physiological structures between applied points are so complicated, moreover, in constant movement, change, and interaction, and in addition, internal potentials and currents are involved, and as a result of all those internal processes, the summary level of the produced energy can not be actually simply calculated, but can be assessed by measuring of the resultant current in an external short circuit. Thus, the obtained value of the generated current reflects not just the physiochemical nature of the electrodes, but also the whole complexity of current conditions of biological substance of the human body between the applied electrodes.

In accordance with the concept of data generation, to produce the data, polarizable electrodes are to be applied to the human body: a number of the meridian electrodes to the certain points on the human body, where the meridians start, and one electrode, which is common for all of the meridians, is to be applied to the common point, e.g., the stomach area. Thus, a number of sources of energy is created: each one is comprised of one meridian electrode, the common electrode, and the inner part of the human body between those two. The number of measured generated currents creates what is called in the present invention primary data.

In terms of specific accomplishment of the primary data generation, the preferred embodiment of the system uses the following particular arrangements: The meridian electrodes are a number of sets of electrodes. The electrodes of different sets may be made of polarizable material (such as Cu or Zn), or, which is in more frequent use, made of Ag-AgCl, or may be made of non-polarizable material (such as C). In the latter case, the common electrode must be made of polarizable material, so that to create the condition for energy generation at least one of the electrodes involved in the source of energy must be made of polarizable material. In addition to the materials specified above, other materials can be used, so long as they produce the well-known effect of galvanization when placed in electro-chemical solution.

The common electrode, in turn, is made of either polarizable material, or non-polarizable (it can be applied either on a layer of a conducting gel, or on a piece of conducting material, soaked in physiological solution.) If the common electrode is non-polarizable, the meridian electrodes must be polarizable.

As would be known to a person of skill in the art, instead of one common electrode, a plurality of separate electrodes could be provided, each associated with a meridian electrode. Also, any combination of meridian electrodes and common electrodes could be used, i.e., several meridian electrodes could use one common electrode, some meridian electrodes may be associated with only one return electrode, multiple common electrodes could be used, etc.

The locations of points of electrode application are determined by locations of points-sources of the corresponding acupuncture meridians, which are located at the extremities. For instance, the "Shenmen"(C7) point, which is located on the skin crease of the wrist on the ulnar side of the flexor carpi ulnaris muscle, represents a source point of the heart meridian. As far as the 12 basic meridians are taken into consideration in this embodiment, and each of them has a corresponding meridian on the symmetrical part of the human body, 24 meridians are tested. Thus, 24 meridian electrodes are applied, 24 sources are created, and 24 channels of data acquisition are required.

Figure 2:
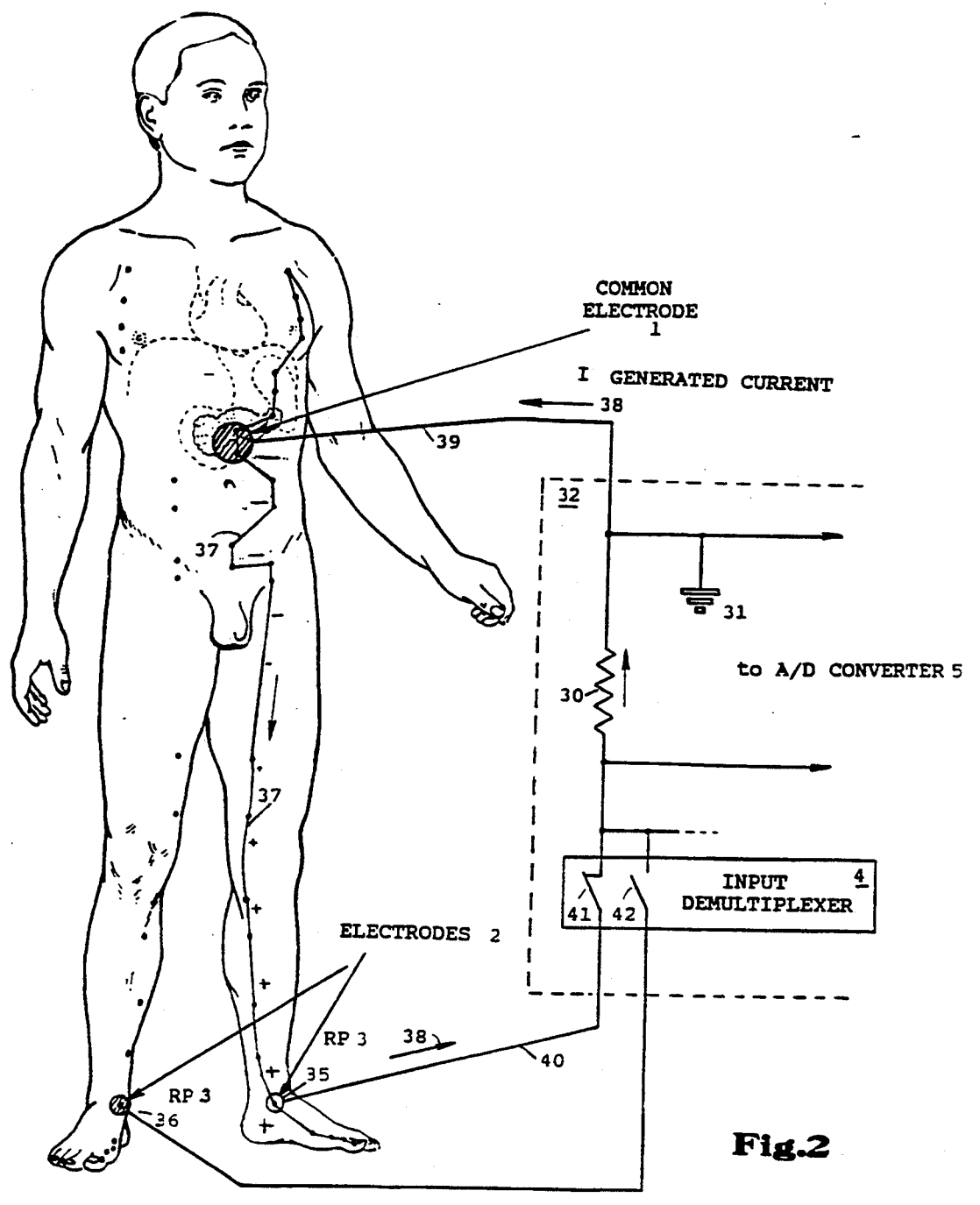
FIG. 2 schematically shows the human body energy source formation, the channel of energy flow and resulting current in the external circuit, involving elements of the measuring circuitry of the invention.

FIG. 2 schematically shows a part of one of the channels of data acquisition for a spleen-pancreas meridian. A common electrode 1 is placed on the stomach area, and a spleen-pancreas meridian electrode 35 is placed on a "source-point" located on the left foot (a corresponding "source-point" 36 is shown on the right foot). These electrodes and inner structures of the human body, between them and along the meridian 37, form the source of energy, which creates a current (I) 38 in an external circuit comprised of electrode wires 39 and 40, a measuring resistor 30, and a sampling switch 41 of an input demultiplexer 4. A current flow creates a voltage across the resistor 30. The value of the resistor 30 is to be at least 5 to 10 times less than the resistance of the human body between the points of electrode application, which is normally in the tens of kiloOhms. The voltage is to be measured by an analog-to-digital converter 5 (FIG. 1). When another switch 42 of the demultiplexer 4 is engaged (so the switch 41 is disengaged), a current generated by the right side corresponding source is to be measured in the same way.

Other equivalent methods for determining the current created by each electrode pair can also be used, instead of the dropping resistor 30. For example, a Hall, effect sensor can also be used to measure the current, as known to those of skill in the art.

2. Data acquisition-B.E. Scan

As shown in FIG. 1, the system comprises broadly of the following major functional units: 24-channel electrodes 2, a point-search electrode 3, common electrode 1, a main data acquisition unit 32, a portable data acquisition unit 27, and a computer unit 33.

Data acquisition (Bio-Energy-Scan - B.E. Scan) is provided by the 24 electrodes 2, the common electrode 3, a resistor 30, input demultiplexer 4, analog-to-digital converter 5, output demultiplexer 6, opto-transmitting unit 8, power supply units 13, 14, and 15, and computer unit 33, controlling the whole main data acquisition unit 32.

As it has been described earlier, a flow of current is generated in the following complete circuit: ground 31, common electrode 1, inner structures of the human body, one of the 24-channel electrodes 2, one of the switches of input demultiplexer 4, measuring resistor 30, ground 31.

The voltage, created by the current in the resistor 30, is measured by the analog-to-digital converter 5. Besides performing the measurement, the converter 5 carries out a conversion of the analog signal into a corresponding parallel digital code.

The parallel digital code is rendered into a serial digital code by an output demultiplexer 6. A purpose of the last conversion is to make it easier to perform a transmission of the digital data to a computer 17 via an optical signal transmission channel.

The input 4 and output 6 demultiplexers are controlled by counters 10 and 11, which serve as address setting units for the multiplexers. The counters are monitored by the computer 17 through a control opto transmitter unit 9, and a control unit 12. The specific embodiment of the described measuring system, comprised of input and output demultiplexers, A/D converter, control unit and counters, depends on the type of A/D converter employed. For example, some of the converters have all of the elements of the measuring system (multiplexers, address units, control units) preinstalled.

The demultiplexers might be a part of one analog-to-digital converter microchip. The counters shown and part of the control unit can also be part of the microchip (some A/D converter microchips have those units preinstalled).

The process of data acquisition is as follows. According to the working program, at a certain moment the computer 17 sends a reset impulse to the counters "1" (11) and "2" (10), thus setting all units into a starting position. Then, count impulses set the counter "2" (10) into a position corresponding to channel #1. The output digital code of the counter "2" (10) sets the input demultiplexer 4 in such a position that an input #1 of it is connected to its output, thus connecting the electrode of channel #1 to the measuring resistor 30. The complete circuit is made, and the A/D converter measures the voltage which is due to a flow of current through the measuring resistor 30. The output parallel digital code of the A/D converter is converted into serial digital code by output demultiplexer 6 : the counter "1" (11) counts reading impulses from the computer 17, consecutively connecting one by one of the parallel outputs of the A/D converter 5 to the single output of the output demultiplexer 6. After the output parallel code of the A/D converter 5 is read, the carryout impulse of the counter "1" (11) sets the counter "2" (10) into a position corresponding to channel #2. Now the output code of the counter "2" sets the input demultiplexer 4 in a position such that its input #2 (and so the electrode of channel #2) is connected to the measuring resistor 30. The whole process of data reading is repeated until all 24 channels are consecutively connected to the measuring resistor 30 and the obtained data are stored in the computer's memory. Thus, the data array of the inner energy "snap-shot" of the human body is ready to be processed and the BioEnergyGram can be developed.

The time of measuring of the current of one channel is chosen in such a way that the current would be stabilized after the measuring complete circuit is made, so it would be an integrated value, close to the real one. The whole process of measurement of the 24 channels may take a few seconds, e.g., 5 to 20 seconds, although of course, the measurements can be taken faster or more slowly, depending on the hardware and software used.

A power supply unit comprises a low voltage converting power supply and consists of a low voltage AC generator 15, a low AC voltage transformer 14, and a power supply unit 13.

A purpose of the whole supply unit is not just supplying the measuring unit with the necessary voltages, but also to perform some safety functions.

The measuring system 32 has a shock protection line 7, which lies through the low voltage transformer 14, the optical transmitting output unit 8, and the control opto transmitter unit 9. In the last two units, electrical signals will be converted into light impulses, transmitted to optical receiving elements through air and converted by the last ones back into electrical signals. The windings of the low voltage transformer 14 preferably are made in such a way that isolation between them can withstand a testing voltage up to 4 kilovolts. Thus, there is no hard-wire connection between the whole measuring unit 2 and the computer unit 33 (the ground 31 of the measuring unit 32 and the ground 34 of the computer unit 33 are different, shown differently and have no connection). This eliminates any hazard to the human organism which may result from currents flowing in such a hard-wire connection, including the possibility of shock due to high voltages of the display monitor 22 and the 115V AC line power or other line power.

The "Shock Protection Line" can be implemented using either isolating transformers or optocouplers, or both. The low Voltage AC Transformer, which is designed for the power supply of the whole measuring unit, is a part of the "Shock Protection Line" and should be of special design (complete separation of the windings and special high voltage isolation therebetween).

A point-search electrode 3 is provided in a pen shape and the tip of it is made of the same material as the 24-channel electrodes. Thus, being applied to the human body, the point-search electrode 3, along with the common electrode 1, can form a source of energy at any point of the body, i.e., wherever the electrode 3 has been applied.

Acupoints have an ability to produce higher levels of energy than the areas around them. Thus, a point-search electrode can be used for finding the exact locations of the acupoints on the human body. Data taken with the help of electrode 3 are processed in the same way as the data from the 24-channel electrodes and displayed on the display monitor 22. Thus, by moving the electrode 3 in the area of a supposed acupoint and observing a current value of the generated current on the display monitor, the exact location of the searched-for acupoint can be found as the spot of the highest obtained readings.

Yet another purpose of the point-search electrode is to perform the data acquisition in a step-by-step order mode, moving from one acupoint to another. There is a push-button on the search-point electrode, and at the moment when the obtained current readings on the display monitor have reached the highest value, i.e. the electrode is positioned exactly on the acupoint, the push-button of the applied search-point electrode is to be pressed at that precise instant, thus giving the computer a command to store the current data in its memory as data, which represent the level of energy of the corresponding meridian. This mode of data acquisition is used in some applications of the present invention.

Instead of the point-search electrode, another kind of input device, a tracer electrode, can be used. A tracer is an electrode having a small free-wheeling active part. The wheel is made of the same material as the active end of a search electrode, and therefore, in combination with the common electrode and when included in the measuring circuit, creates the same kind of source of the energy as any of meridian electrodes or the search electrode. Being placed at the beginning of a meridian, the tracer can be moved along the meridian, automatically taking readings on its way. When crossing specific points on the meridian, a push button, conveniently placed on the tracer, is pressed, thus creating "land marks" of the received representation of a bio-energy distribution map for the particular meridian. The whole map represents a number of graphs. Each graph is a function of level of inner energy and distance along the meridian.

Some diagnosing methods have been tested in combination with assessing of the BEG, obtained by the present system, and EKG, taken at the same moment by a conventional EKG apparatus 23. Therefore, to accomplish simultaneous assessment of both characteristics, the measuring unit 32 includes a fast A/D converter 24. This A/D converter 24 performs differential (i.e. at each time point) input of the cardial muscle impulses versus the integral input timing feature of the A/D converter 5. Instead of the EKG apparatus, a blood oxygen saturation measuring unit may be used.

The computer unit 33 includes the computer 17, a read only memory ROM 21, a display monitor 22, and a power supply "1" 16. The computer 17 performs the working program and the whole process of data acquisition, data processing, all assessments, data storage, developing the BEG, generating a diagnosis and a prescription, and all application programs. The working or any of the application programs may be installed on a hard drive 19 of the computer 17 through the floppy disk drive 18, or be executed directly from the floppy disk drive 18. Also, personal data files are to be backed up on the floppy disks. A tape backup 20 is for large data arrays to be formed for statistical processing purposes. Also, it serves as a data archive for long term research.

A simplified embodiment of the present embodiment might not have either of the disk drives, so the ROM 21 (Read-Only-Memory) may be used, where the basic working program is permanently installed and to be executed automatically directly from the ROM right after the system is turned on.

Some of the recently developed techniques of biotherapy involve a combination of simultaneous application of relocation of the inner energy, massage, and an electromagnetic field on the points, which have been chosen for the biotherapy either by the computer or by the attending physician. For that purpose, a special massaging electrode 25 has been developed, which combines a biotherapeutic electrode and a miniature solenoid attached to it.

A vibro-pulse generator 26 generates impulses of the period and duration set by the physician from the computer's keyboard. The solenoid converts electrical impulses into mechanical vibrating motion, which causes a massaging effect onto the acupoint. According to existing therapy techniques, the small/insignificant electromagnetic field, created by the solenoid's winding, also may provide a therapeutic effect.

A portable data acquisition unit (PDAU) 27, to be described below, is useful in finding the right diagnosis. Being connected to the computer 17 through a port connector 35, it is to be programmed by the physician for the time of data acquisition. Being attached to a patient for that time, which might be from several hours to a couple of days, the unit reads and stores the data from searched acupoints with time intervals between readings set by the physician. On the day of the next appointment, the physician connects the unit to the computer, which initiates transfer of the data collected by the unit into its memory, displays the data on the background of the most recent BEG so that the physician has an ability to judge what is really going on with the suspected abnormality meridians.

In addition to storing the meridian measurements over a predefined time period, the PDAU 27 can also have one or more temperature sensors 44a coupled to the patient so that correlations between the meridian measurements and the temperature readings can be analyzed. Similarly, the main unit shown in FIG. 1 can also have temperature sensors 44b for the same purpose.

Also shown in FIG. 1 are a Z-divider 28 and a microammeter 29. These two units enable the physician to control some of the generated currents from the acupoints without participation of the whole electronic system, even without turning it on. The Z-divider 28 sets the scale of the microammeter 29 into that appropriate for the reading range. Besides the control function, these two units allow observation of the change in current during certain periods of time from electrodes attached permanently. Thus, the circuit of generated current flow is completed for a much longer time than during electronic measurement. These two units have no electrical connection with the rest of the system.

3. Portable Data Acquisition Unit (PDAU)

The Portable Data Acquisition Unit - PDAU - is optional, as is the Vibro-Pulse Generator (VPG), Vibro Electrodes, EKG, and Fast A/D Converter. The PDAU comprises an input demultiplexer, A/D Converter, Timer, Address Counters, Memory, Control Unit, and Ni-Cd battery.

Figure 3:
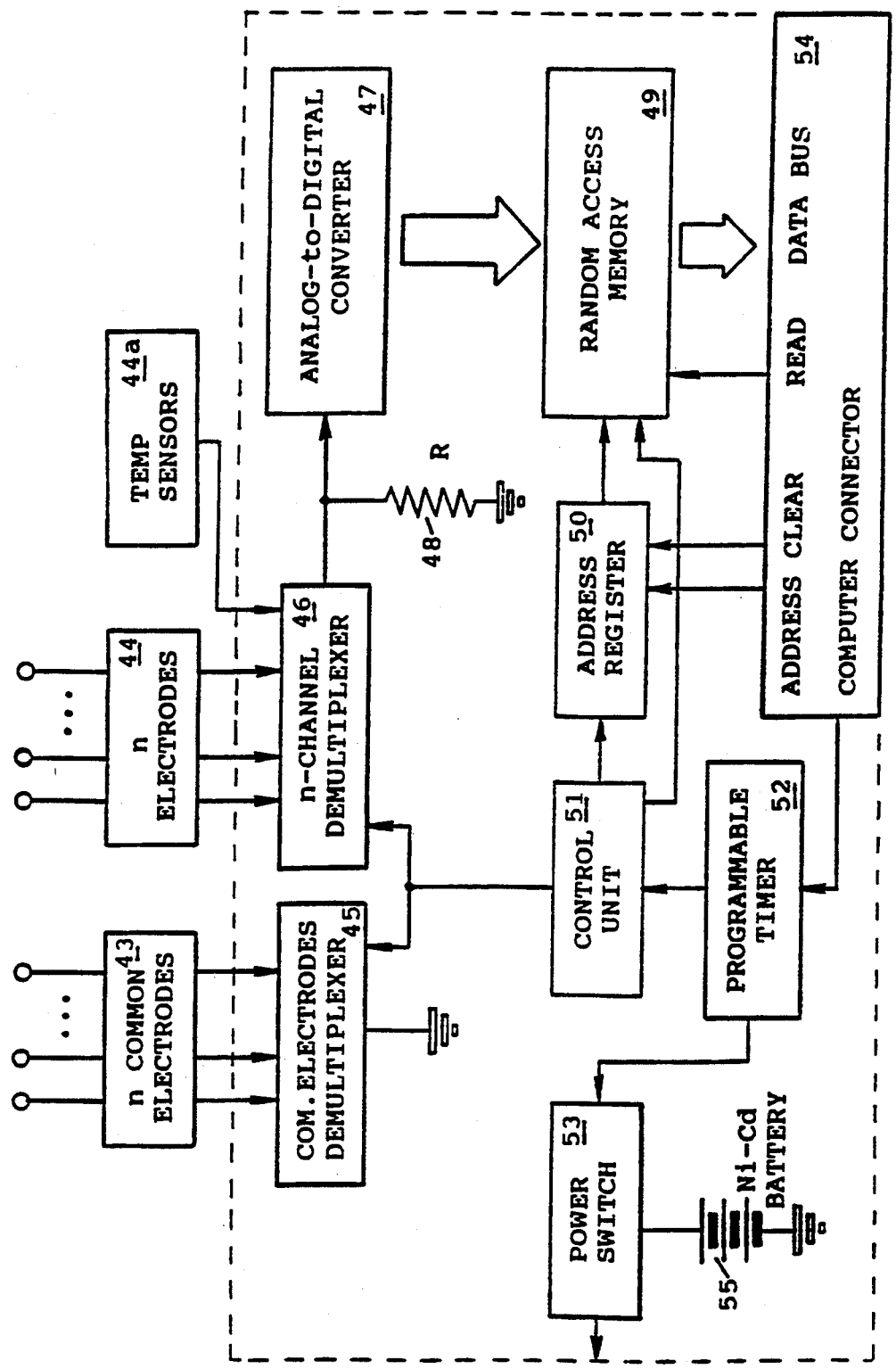
FIG. 3 is a schematic block diagram of the portable data acquisition unit.

FIG. 3 is a schematic block diagram of the PDAU 27. Similar to the main data acquisition unit of the device, the PDAU comprises an A/D converter 47, which measures voltage on a measuring resistor 48. The voltage is due to a current generated by a human body with electrodes applied. The electrodes are to be included in the measuring circuits, which are the same ones that have been described earlier and are shown in FIG. 2, via two demultiplexers: the n-channel demultiplexer 46 and the common electrodes demultiplexer 45. The purpose of the n-channel demultiplexer 46 is the same as the purpose of the input demultiplexer 4 shown in FIG. 1, i.e. to connect participating electrodes 44 to the measuring resistor 48. The purpose of the common electrodes demultiplexer 45 is to give a physician a choice of applying the common electrodes 43 of each meridian-common-electrodes pair separately. This will enable the physician to choose different points of application of common electrodes or give a better way of securing those electrodes on the body, because some disturbances might occur while the electrodes are worn along with the PDAU on the patient's body.

The analog-to-digital converter 47 converts the analog value of the voltage on the resistor 48 into a parallel digital code, which is stored in a random access memory (RAM) 49. A programmable timer 52 generates signals, which are necessary for the control of the whole unit. The timer 52 is programmed in such a way that the time of storage of the RAM 49 will be stretched into the whole desired period of data acquisition. A control unit 51 provides the demultiplexers 45 and 46 with the code to enable them to connect a channel of a certain number, at a given moment of the time. Also, it gives a command "WRITE" to RAM 49 to store the output digital code of the A/D converter 47, which, by that time, has performed the measurement of the current, generated in the channel. After the storage of the information has been carried out, the control unit 51 changes the address in an address register 50 to the next consecutive number, which corresponds to the next channel storage cell address in the RAM 49 so that now it is ready to store the information of the next channel.

After a cycle of measurement of all participating electrode currents has been accomplished, the programmable timer 52 enables a power switch 53 in such a way that, for the purpose of energy saving of the Ni-Cd battery 55, the whole PDAU is disconnected from the battery 55, except the RAM 49, address register 50, and timer 52. When the time of next measurement occurs, the programmable timer 52 enables the power switch 53 to provide all units with power, and the next cycle begins.

After the whole process of data acquisition has been completed, the PDAU is to be connected to the computer through a computer connector 54. The computer provides to the unit control signals, such as "CLEAR" and "READ", to operate the unit. After the unit has been reset by the signal "CLEAR", the computer sets the address and provides the signal "READ" to fetch the data out of the RAM 49 on the "DATA BUS" and to store the data in its memory. Then the computer sets the next consecutive address and takes the next data until all the information is transferred into its memory.

The PDAU can also have inputs from one or more temperature sensors 44a so that correlations between one or more temperature measurements and one or more current measurements can be analyzed. This is often useful in diagnosis.

4. Data processing

The basic algorithm of the primary data processing contemplates the following steps: A mean value of two readings obtained from the corresponding channels (left and right sides of the meridians of the same name) is to be calculated. This mean value will represent the level of energy of the given meridian. Then a mean value of all readings is to be calculated. This mean value will represent the mean level of energy. If one or more of the readings equals zero, the working program aborts calculations, insisting on checking possible bad contact between the corresponding electrode and the skin. If one of the readings is too low or too high, the calculations proceed without taking it into consideration. In case of a very low value of any of the readings, it is also suggested to check the contact. After all data readings are stabilized (the same, steady values after several consecutive initiations for measurement) the system is ready to generate the BioEnergyGram (BEG).

5. Generating Bioenergygram

Generating the BEG is a process of plotting the result of data processing on a special diagram, called a biodiagram. A biodiagram is a chart of relatively placed scales of values of electrical currents generated by a human body from corresponding acupoints of the meridians. The scaling of each relatively placed scale may be different, based upon the measurements obtained via experience. For convenience, it is preferable to arrange the scales in such a way that the meridian values for each scale (each scale corresponding to a meridian) are disposed so that they define a horizontal line around which a physiological corridor is formed.

Such biodiagrams have been obtained through prolonged experiments and statistical assessments of data, obtained during examinations of individuals known to be healthy. The biodiagram is still an object to be explored and, probably, adjusted to different circumstances, such as age, climate, and latitude. In overall cases, however, it has proven to be effective and accurate.

As explained briefly earlier, rather than using complicated calculations (which could also be used as known to those of skill in the art), a well-known research method for building diagrams, and in particular, biodiagrams, is used. The diagram actually is a table, in which the columns include all possible values of the currents for a particular meridian, properly scaled based on experience. The rows of the table represent corresponding values of other meridian currents which have been taken from a person known to be healthy.

|      | meridians (columns) | | | | | | | | | | | mean value of the currents |
|------|---|---|---|---|---|---|---|---|---|---|---|---|
|      | 1 | 2 | 3 | 4 | 5 | 6 | 7 | 8 | 9 | 10 | 11 | |
| rows | 10 | 13 | 24 | 09 | 45 | 34 | 23 | 18 | 16 | 34 | 45 | 24.6 |
|      | 10 | 11 | 23 | 09 | 44 | 33 | 23 | 17 | 15 | 33 | 42 | 20.5 |
|      | 09 | 09 | 22 | 08 | 43 | 32 | 22 | 16 | 14 | 32 | 39 | 17.8 |
|      | 09 | 07 | 21 | 08 | 42 | 31 | 22 | 15 | 13 | 30 | 32 | 16.2 |
|      | 08 | 06 | 20 | 07 | 40 | 30 | 21 | 13 | 11 | 28 | 30 | 14.6 |

The table above is a simplified part of such an imaginary biodiagram. The diagram shows that if a mean value of all currents is 17.8 microAmps (for example), then it is more likely that for a healthy human organism, the current measured for meridian #1 will be 09 microAmps, for the meridian #3 - 22 microAmps, for #4 - 08 microAmps and so on. Thus, the numbers of the row 3: 09, 09, 22, 08, 43, 32, 22, 16, 14, 32 and 39 represent the ratio/correspondence between the currents generated by the particular individual known to be healthy whose mean value of all generated currents is 17.8 microAmps. These values can be represented on the biodiagram, for convenience, by appropriate scaling of each scale corresponding to a meridian, so that the values define a straight horizontal line. The rows above and below could be considered as comprising an imaginary physiological corridor. That means that 10 microAmps for meridian #1, or 21 microAmps for meridian #3, or 32 microAmps for meridian #11 could be considered as normal (within specification). So, a single value of 23 microAmps for meridian #3 does not tell one much, but if we have a mean value of all currents from all meridians equal to 20.5 microAmps, it is obvious that the current is within normal range. On the other hand, if a mean value is 14.6 microAmps, the value of 23 microAmps for meridian #3 is too high for that particular meridian (should be close to 20).

From the above example, it is obvious that the relation between absolute values of the currents is represented by mutual location of numbers in the table shown above. So, although the absolute value of currents is measured and, those absolute values are plotted on the biodiagram, an assessment of how close to the standard location (how close to a horizontal row) they are is predetermined by a relative disposition of numbers in the diagram/table with respect to a mean value of all the current values.

Accordingly, as described, the scales of a biodiagram are placed vertically in such a relation that any horizontally drawn line intersects the scales at points, which combine an array of data of a healthy human organism. Even though a body of a particular individual known to be healthy can generate a different amount of energy at a different time, as well as different healthy individuals have different abilities in that sense, the final picture is the same: the data being plotted on the scales ideally and for convenience in using the biodiagram lie on one horizontal line. Therefore, even for a particular healthy individual, although the line might be higher or lower on the biodiagram, depending on the particular condition of the person's body, it should nevertheless be a horizontal line. The very fact of data location on the straight horizontal line regardless of its current position on the whole biodiagram represents the very concept of the balance of inner energy generated by a healthy human body.

Even human bodies known to be healthy are not perfectly ideal. Therefore, it is practically impossible to obtain an ideal BEG, which is a straight horizontal line. On the other hand, there are some errors in measuring the data, due to inexact locations of the acupoints, for example. Thus, there are some deviations of data location, but for healthy organisms all of them lie in a certain range, close to the horizontal line on the BEG. The possible values of the currents of the healthy human body under certain conditions and at a certain moment form a physiological corridor, within which all the values lie. On the biodiagram, the corridor is located between two horizontal lines, above and under the central, "ideal" BEG, and "moves" up and down on the biodiagram along with the "ideal" BEG line.

6. Types of BEG

Figure 4A:
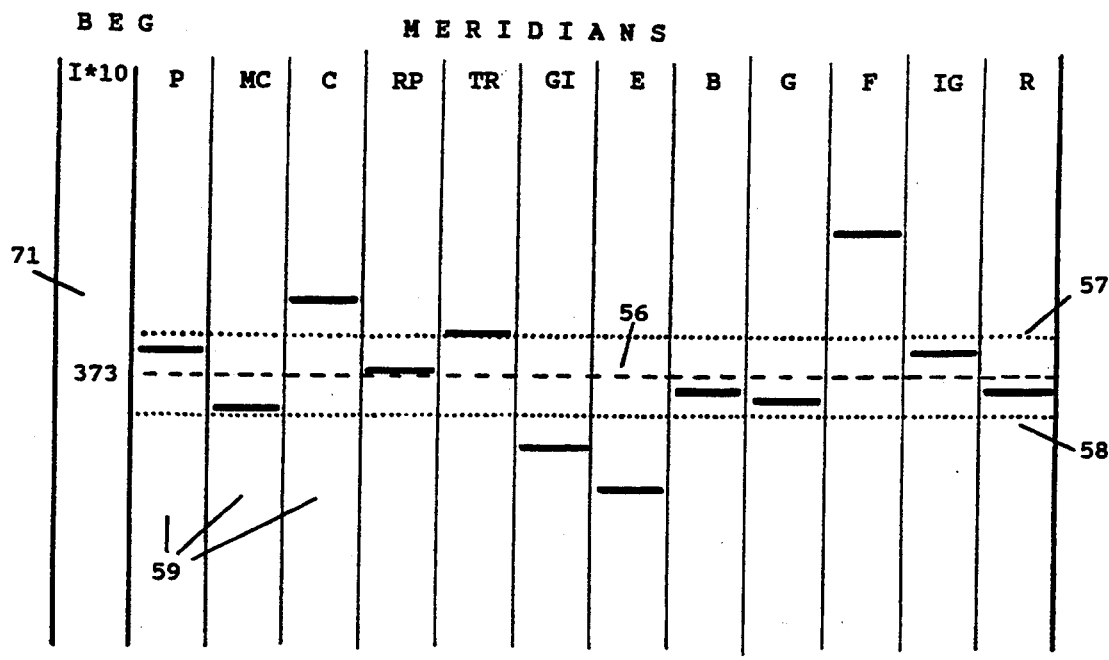
FIG. 4a is a variant of the Bio-Energo-Gram (BEG) display know as a step BEG.
Figure 4B:
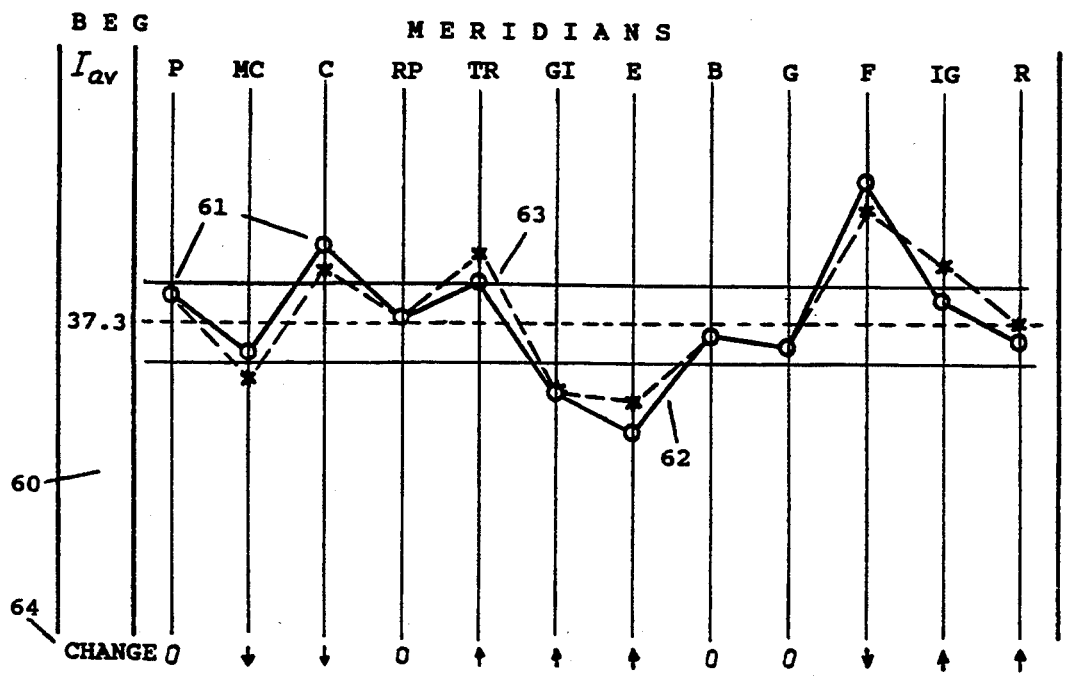
FIG. 4b is variant of the BEG display known as a continuous BEG.

Concrete examples of BEGs are shown in FIG. 4a and FIG. 4b. Also, FIG. 4a and FIG. 4b represent two of the possible variants of a software output, i.e. a picture of a BEG on the screen of the display monitor.

FIG. 4a shows a step variant of the BEG of a probable individual. Such a variant enables a physician to assess more easily the levels of a person's inner energy visually. The left column 71 represents a scale of a mean value of the whole amount of inner energy multiplied by ten. For the sample, shown on FIG. 4a, the measured and calculated mean value is 37.3 mA, so the number is 373. 12 vertical columns 59 represent the scales of possible values of generated currents in the channels, corresponding to the 12 major meridians. A horizontal line 56 is the described earlier ideal BEG of a potentially healthy human body. Accordingly, this line is drawn on the level of the number 373 and represents an ideal BEG of the particular individual at the present condition as if the person were perfectly healthy. Two horizontal lines, 57 and 58, represent a tolerance energy level above and below the ideal BEG 56. A space between lines 57 and 58 is the physiological corridor for the particular individual.

The measured, real levels of inner energy in each channel are shown by short horizontal lines within each vertical column, so comprising the steps of the step BEG. As it can be derived from the sample BEG of FIG. 4a, the level of inner energy of the channels P, MC, RP, B, G, IG, and R are within the specification of the tolerance of the physiological corridor. Meridians C and F have excessive levels of inner energy, and meridians GI and E have insufficient levels of the energy. So, the first two are called excited meridians and the second ones are called depressed meridians.

A continuous variant of the BEG is represented in FIG. 4b. The continuous BEG enables a physician to assess dynamics of the balance of the inner energy under different circumstances, i.e. changes, which might occur, for instance, either under influence of some external trial action, as providing biotherapy might be, or due to natural inner processes in the body with the passage of time. The continuous BEG is plotted on the same biodiagram as the step BEG. The differences are that the mean value of the overall level of inner energy, which is to be displayed in the right column 60, should not be multiplied by ten (in the shown instance, it is 37.3), and levels of the inner energy are shown as points on the vertical scales 61 (not lines). All the points are connected consecutively in one continuous line 62, which comprises the continuous BEG.

The different continuous BEGs, taken at different times and under different or the same circumstances, are preferably shown in different colors, for instance, BEG 62 is red, and BEG 63 is yellow. The number of simultaneously shown BEGs may vary and depends on the discretion of the physician. Preferably, an automatic mode is preserved to display consecutively all BEGs of the particular individual in dynamics of fading brightness of the BEGs as the brighter recently taken BEG appears on the screen.

A line "CHANGE" 64 in FIG. 4b shows the most recent change in the last BEG appearing on the screen in comparison with the previous one.

Another example of a continuous BEG is shown in FIG. 5. It comprises two axes: X-axis 65 represents different circumstances of particular data acquisition, as the different times might be, and Y-axis 66 represents the scale of the level of inner energy, scaled in microAmperes.

FIG. 5 shows a continuous BEG of a PDAU as data collected by the unit during 26 hours and plotted on the ground of the physiological corridor of one of the previously taken BEGs, whichever the physician prefers. Each continuous line represents one of the meridians, which have been chosen for the search. For example, FIG. 5 shows that among three of the searched meridians, MC (69), VB (68), and F (67), the concern is about the VB meridian because the other two are in the specification of the physiological corridor 70 most of the time.

Different application programs process the data differently, specific for each program, so the software output may differ and serve the specific task of the particular program. A hardware output, for example, a printout, might be a copy of any software output, or it might be statistical tables or diagrams. Typical software outputs might be a graph, reflecting the primary data plotted on the biodiagram, i.e., the Bio-Energo-Gram-BEG.

Figure 6A:
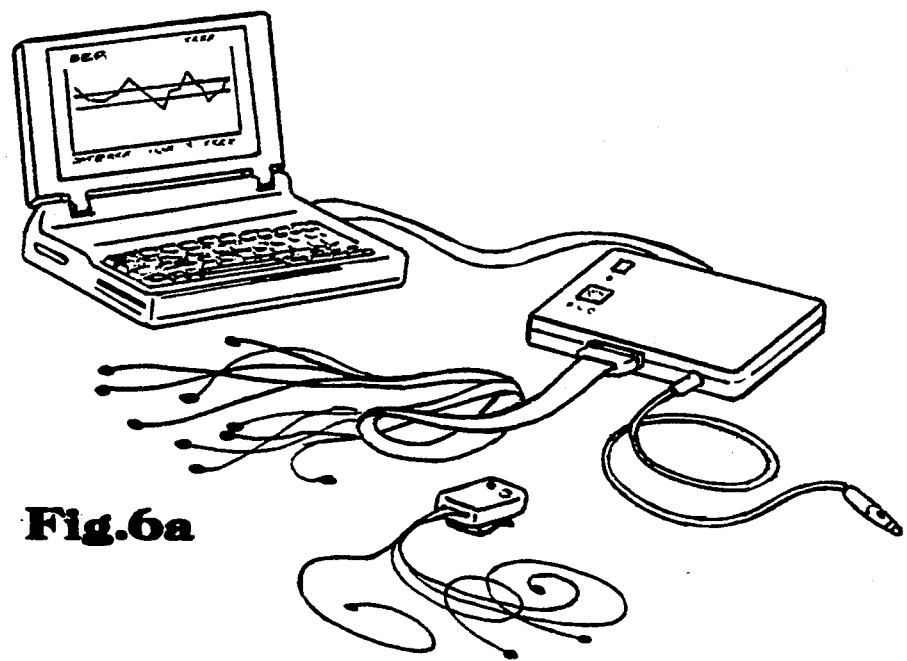
FIG. 6a shows an embodiment of the system based on a separate measuring unit and a lap-top computer.
Figure 6B:
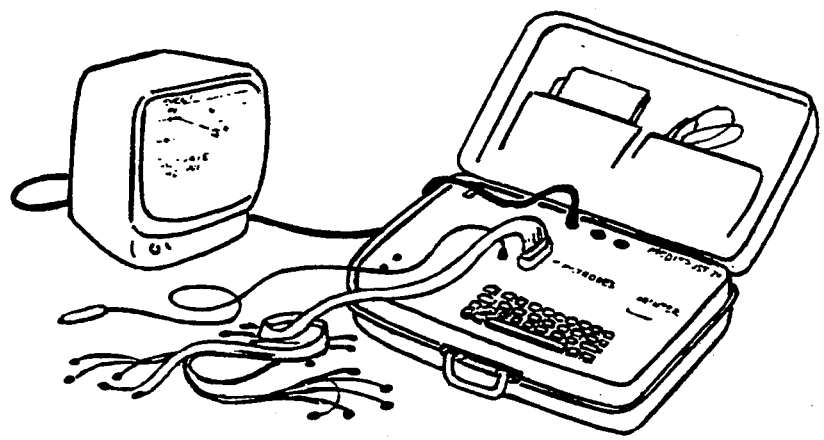
FIG. 6b shows a portable embodiment of the system, combining measuring unit and computer in one case.
Figure 6C:
FIG. 6c shows an embodiment, based on a separate measuring unit and desk-top computer.

FIGS. 6a, 6b and 6c show different hardware embodiments of the invention as will be apparent to those of skill in the art.

Figures 1, 7A:
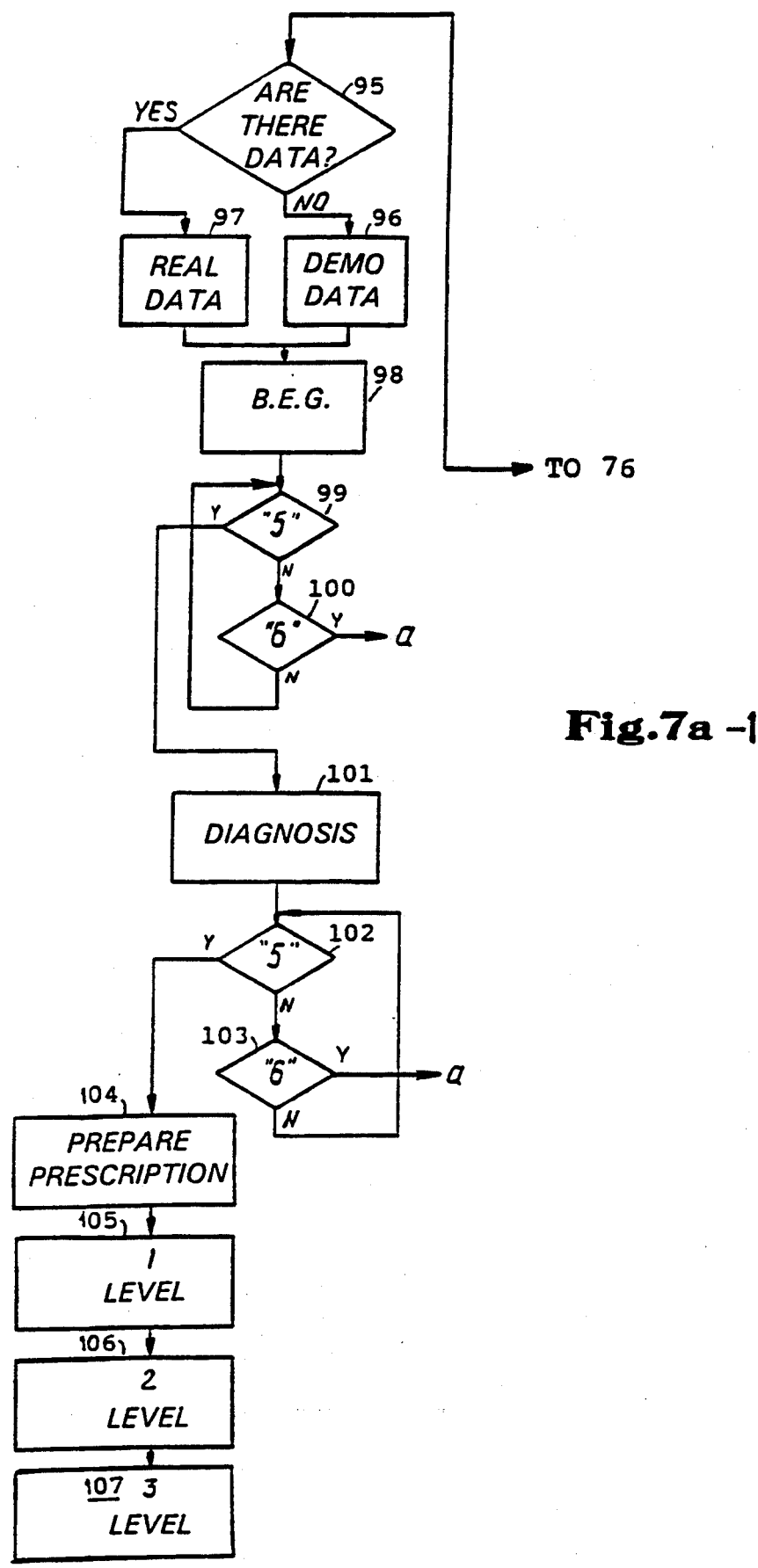
FIGS. 7a and 7b show a flowchart of an embodiment of the basic operating system computer software used in the present invention.
Figures 2, 7A:
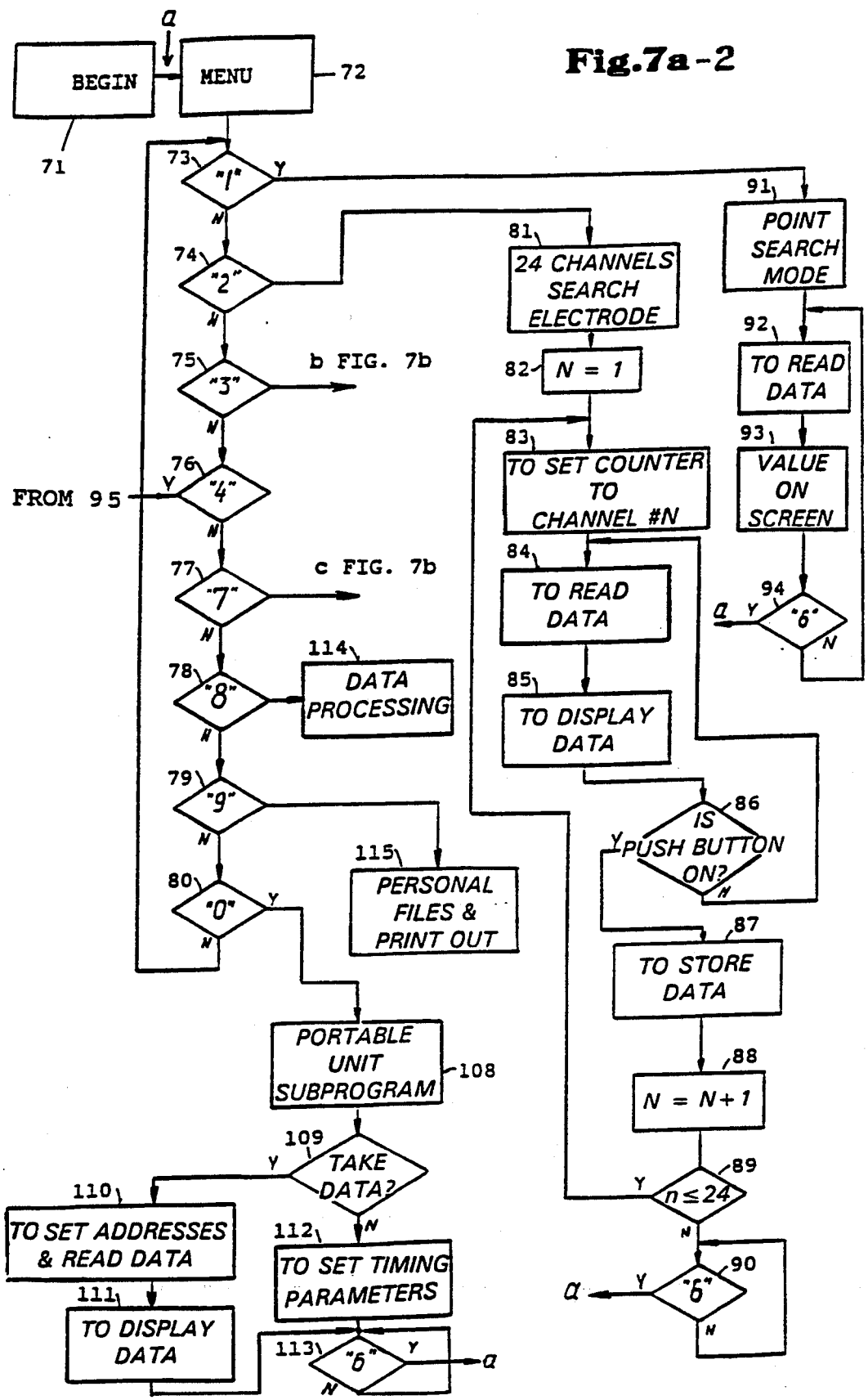
Figures 1, 7B:
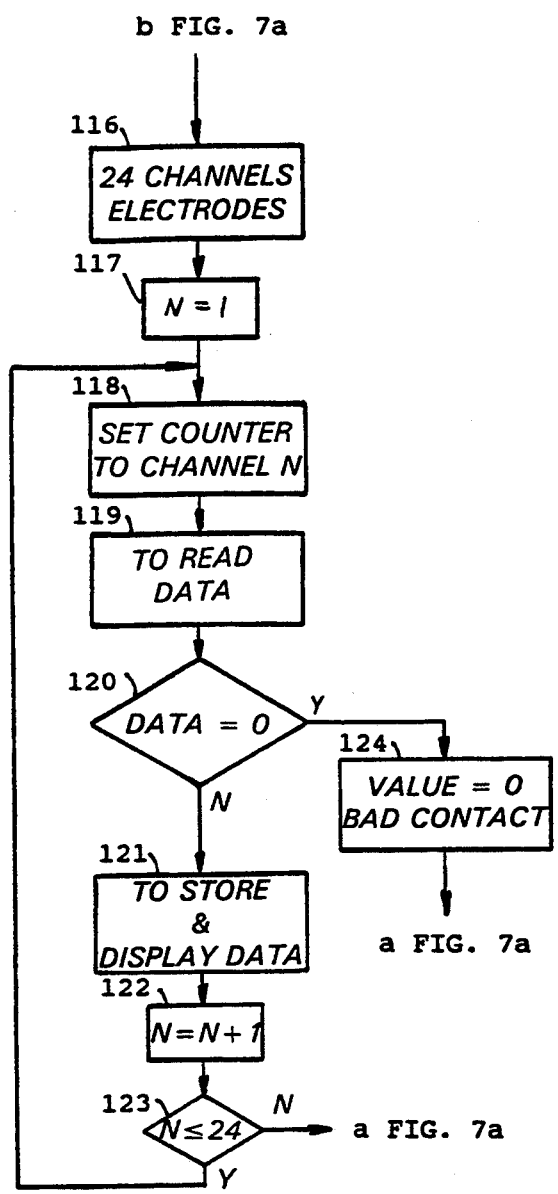
Figures 2, 7B:
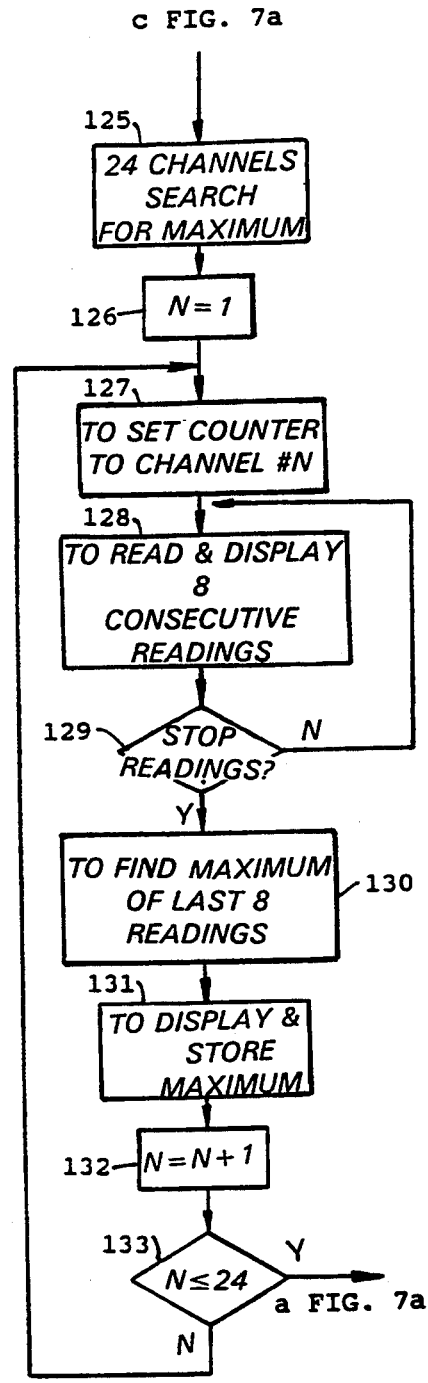

FIGS. 7a and 7b show one embodiment of the basic operating program of the invention.

7. Basic Operating Program

The particular variant of the operating program depends on the objective of the particular embodiment. One program can be designed for a portable unit, based on a lap-top computer, and serves to obtain the data either at the patient's residence or any location outside the doctor's office. On the other hand, a system designed for profound medical research, is to be provided with a powerful data acquisition program with all features of large data arrays processing and statistical tools.

Yet another aspect of building an application program for the system is that a growing number of new areas, where the system is deemed to be applied, constantly demand either modification of already existing particular application programs, or building absolutely new programs in terms of data interpretation. For example, changing an approach in setting a diagnosis, or the number of tested meridians could be increased (as it has been mentioned before, there are two more "unsymmetric" meridians) or decreased.

Besides some application differences in generating a program for the system, there are different programming languages that can be employed. For instance, programs can be written in ASSEMBLER and PASCAL, and a program written in C++ has been developed.

FIGS. 7a and 7b represent a flow chart of one embodiment of the basic working program.

The flow chart begins with BEGIN block 71. After the execution of the program has been started, MENU 72 is to be displayed to give a user an option as to which way to proceed:

"1"—point search mode: allows determining the exact locations of the acupoints with the help of the search electrode;

"2"—24-channel search electrode mode: designed to accomplish the process of data acquisition in step-by-step order (point-to-point method) with the help of the search electrode;

"3"—24-channel, snap-shot mode (major mode): allows taking the data from all the acupoints, where the 24 electrodes have been attached, simultaneously (within a few seconds);

"4"—BEG generating mode: data processing; activates mode "5";

"5"—diagnosis and prescription mode: generates diagnosis and acu-/bio-prescription;

"6"—back-to-menu mode: returns program to the start point from any current point of the program;

"7"—24-channel search-for-maximum mode: same as "2", except the maximum value of several, e.g., eight last readings is taken as a true value;

"8"—data processing mode: includes a number of operations with data taken before; for example, previously taken BEGs are to be displayed in automatic or semiautomatic mode;

"9"—file/print mode: file operations (saving, deleting, getting, etc.); printout;

"0"—PDAU mode : works with the portable data acquisition unit.

A point-search mode is to be executed when it is selected from the MENU. A block 73 represents a general relational structure IF-THEN-ELSE, which directs/redirects the flow of the program if a contained boolean expression is TRUE or FALSE. For example, IF mode "1" is to be chosen ("GO TO POINT-SEARCH MODE" is TRUE), THEN the next block to be executed is the block 91 ("Y"—stands for YES in that case). Otherwise, IF the mode is not selected, the value of the expression is FALSE and control is to be transferred to a block 74 of the program, which, in turn, is another relational block. All diamond-shaped blocks in the flow-chart are of the same function.

In the point-search mode, the computer reads the data continuously (92) from the point-search electrode. The values of the readings are displayed on the screen in a form, convenient for visual perception (93): that is, a consecutive row of vertical lines, the length of which is proportional to the values. The described process continues until a key "6" (BACK-TO-MENU) is pressed (94).

If 24-channels search electrode mode has been chosen (74), a corresponding part of the program is to be executed (81). "N" is the number of a channels that have currently been tested. Block 82 sets "N" equal to 1, i.e. channel number 1. Block 83 sends a proper signal to the output port to set channel counter to "N". This mode of the program is designed to obtain all the 24 readings with the help of search-point electrode in step-by-step mode. Thus, in step one, it is deemed that the electrode is positioned in the area of the suggested location of the acupoint, corresponding to channel number N=1. Blocks 84 and 85 work in the same manner as already described blocks 92 and 93, except that the readings are displayed in their numeric value. The process of continuous measurement continues until the highest value of the readings has been reached (i.e. the exact location of the point has been found), and a physician decides to press the push button on the electrode while keeping it on the found point location (86). Thus, the value, representing the level of current generated from the channel, is to be stored in the corresponding location in the memory of the computer (87). The step 1 is now over.

Then number "N" is to be increased by 1, i.e. number of the following consecutive channel is defined (88), and if it is not less or equal to 24 (89), which means it has not been the last channel, the program loops to the block 83, and step 2 begins. After all 24 steps are accomplished, N becomes equal to 25, which is more than 24, and block 89 directs a flow of the program to block 90. At this moment, the data corresponding to all 24 channels have been stored in the memory, and after block 90 returns the program back to the menu, it is possible to process the data in the desired way.

A similar process of obtaining the data is to be performed by the program when mode "3" of 24 channel electrode measurement has been chosen (75). It is assumed that all the exact locations of the acupoints have been found (for example, using the described point-search search mode "1") and all 24 electrodes have been placed on the locations. The difference is that the program in this mode performs all 24 steps automatically, going from one channel to another as soon as the measurement of the generated current from the particular channel has been done. Thus, in a matter of several seconds all data are obtained and represent a "snapshot" of the balance of inner energy of the tested human body. Block 116 (FIG. 7b) starts the mode, and block 117 sets "N" to 1. Block 118 is the beginning of the loop, during execution of which all 24 measurements are to be done, the obtained data are stored in the memory and, at the same time, displayed on the screen. The loop consists of blocks 118, 119, 120, 121, 122, and 123. Block 120 checks if any of the read values is equal to zero. If "yes", the program stops the process of data acquisition and goes out of the loop to block 124, which provides on the screen a suggestion to check the contact of the corresponding electrode and turns the program flow back to the menu.

The 24-channel search-for-maximum mode "7" is to be executed from a program point presented by block 77 (FIG. 7a) to block 125 (FIG. 7b). All measurements are to be done in a mode similar to the block number "2", i.e. with the help of the point-search electrode. The difference is that in this mode, the 8 last consecutive readings, corresponding to the particular channel, are always under control (128) until after the physician presses the push-button on the electrode (129), which means that he has found the exact location of the searched acupoint and believes that the true value is among the last 8 readings. Then the computer determines the maximum value of the last 8 readings (130), stores it in the memory, and, simultaneously, displays it on the screen (131). Block 132 forms the next consecutive channel number, and block 133 determines whether it has read the last channel. After all 24 channels have been tested, the data array is formed and is ready to be processed. Block 76 directs the program flow into the major data processing mode "4", generating the BEG with the further data interpretation.

If there have not been any data collected, block 95 fills an active current data field in the memory with a demo file (96). The file is designed for demonstration purposes. If there are real data, the program works with it. Then, according to the algorithm described earlier, the program generates the BEG (98). After the BEG has been generated, there are two choices, which are either to proceed with providing a diagnosis and generating a prescription (99), or to go back to the main menu (100).

Block 101 of the program evaluates the BEG and provide a bioenergy diagnosis, which reflects conditions of the tested meridians. There have been developed medical pre-diagnoses based upon results of the obtained BEG. The matter of providing an exact diagnosis is, of course, in the discretion of the physician who is using the system. Pre-diagnosis is not included in the basic program. Blocks 102 and 103 allow either continuing with the prescription or returning to the main menu.

Block 104 starts generating an acuprescription. Blocks 105, 106 and 107 generate three different prescriptions, based on three different approaches of assessment of the interaction of inner energy carriers in the human body. Mode "8" is designed to process the obtained data in several different ways. For example, a continuous BEG can be displayed instead of a step BEG, or all recently taken BEGs could be displayed, or changes in one particular meridian could be displayed.

Mode "9" is a standard block for any computer program, which works with files and print-outs. It performs the following actions with files: saving, deletion, getting, inserting. Also it allows printing out particular data or the BEG.

The basic working program might not have a subprogram for the portable data acquisition unit (108). It depends on the particular embodiment of the system.

The mode "0" (80) performs working with the PDAU. Block 109 allows directing the program flow either to setting the unit for intended time of data acquisition (112), or to transfer data already collected in the PDAU into the computer's memory (110) and to display the data on the screen (111).

Although the present invention has been described and illustrated in detail, it is clearly understood that the same is by way of illustration and example only and is not to be taken by way of limitation, the spirit and scope of the invention being limited only by the terms of the appended claims.

What is claimed is:

1. Apparatus for assessing the physical condition of an organism, comprising:

means for receiving inputs from a plurality of electrode pairs appliable to the organism, at least one of the electrodes in each electrode pair being polarizable and an electrode in each pair being of a different material than the other electrode in the pair, an electrical current thereby being generated between the electrodes in each pair when applied to the organism;

first means for determining the electrical current between the electrodes in each pair so as to obtain a plurality of current measurements;

means for comparing the determined electrical current for each electrode pair with a respective value for each electrode pair corresponding to an organism known to be healthy;

second means for determining if said electrical current for each electrode pair is within an acceptable range of the respective value for each electrode pair corresponding to the organism known to be healthy; and means for assessing the physical condition of the organism based upon the relationship of the electrical currents to the acceptable range.

2. The apparatus recited in claim 1, wherein:

said means for receiving comprises means for receiving inputs from a plurality of site-specific electrodes and one common electrode, thereby to provide a plurality of current sources, each current source between a respective site-specific electrode and said common electrode defining an electrode pair;

said first means comprises means for determining the electrical current generated between each of said plurality of site-specific electrodes and said common electrode;

said means for comparing comprises means for comparing said electrical current for each electrode pair with a respective value for each electrode pair corresponding to an organism known to be healthy;

said second means comprises means for determining if said electrical current for each electrode pair is within an acceptable range of the respective value for each electrode pair corresponding to the organism known to be healthy; and said means for assessing comprises means for assessing the physical condition of the organism based upon the relationship of the electrical currents to the acceptable range for each of the electrode pairs.

3. The apparatus recited in claim 2, wherein the first means comprises means for determining an electrical current value by measuring a voltage.

4. The apparatus recited in claim 2, wherein the means for comparing comprises means for generating a bioenergygram displaying a plurality of ideal measurements derived from a statistical assessment of data from measurements of healthy organisms, said ideal measurements defining a physiological corridor delimiting said acceptable range, and displaying the current measurements from each of said electrode pairs; and said means for assessing comprises means for providing a diagnosis if any of said electrical currents is outside said physiological corridor.

5. The apparatus recited in claim 2, wherein the first means comprises means for determining said electrical currents for each of said electrode pairs sequentially in time.

6. The apparatus recited in claim 2, wherein the first means comprises means for determining said electrical currents for each of said electrode pairs substantially simultaneously.

7. The apparatus recited in claim 2, wherein said site-specific electrodes comprise electrodes adapted to be applied to particular points of the organism.

8. The apparatus recited in claim 7, wherein the electrodes comprise electrodes adapted to be applied to particular points of the organism in accordance with the practice of Oriental medicine.

9. The apparatus recited in claim 2, wherein said means for comparing further comprises means for generating a bioenergygram charting measurements of each of said electrode pairs versus said value for each electrode pair corresponding to an organism known to be healthy.

10. The apparatus recited in claim 9, wherein said means for generating a bioenergygram charting measurements of each of said electrode pairs comprises means for relating said electrode pair measurements to a specific meridian of the organism corresponding to a meridian from the practice of Oriental medicine.

11. The apparatus recited in claim 10, wherein said means for generating a bioenergygram comprises means for forming a step bioenergygram wherein the electrode pair measurements are plotted as a plurality of discontinuous lines corresponding to each meridian.

12. The apparatus recited in claim 10, wherein said means for generating a bioenergygram comprises means for forming a continuous bioenergygram wherein the electrode pair measurements are plotted as a plurality of connected points corresponding to each meridian.

13. The apparatus recited in claim 10, further comprising means for determining the electrical currents from said plurality of electrode pairs over a predetermined time period, and means for generating said bioenergygram for said predetermined time period, said bioenergygram comprising a plurality of graphs charting the current generated by each electrode pair over said predetermined time period.

14. The apparatus recited in claim 13, further comprising portable means for determining the electrical currents during said predetermined time period.

15. The apparatus recited in claim 14, wherein said means for comparing, said second means and said means for assessing comprises a computer having appropriate software and further wherein said portable means comprises:
    demultiplexer means for sampling the currents from each of said electrode pairs;
    a resistance coupled to the demultiplexer for passing the current from each electrode pair and converting the current to a voltage drop;
    an analog to digital converter for measuring the voltage across the resistance corresponding to each electrode pair and converting the voltage to a digital signal;
    a memory for storing the digital signal from the analog to digital converter;
    control means for controlling said demultiplexer means and memory; and
    interface means for coupling said memory to said computer.

16. The apparatus recited in claim 15, wherein said common electrode comprises a plurality of common electrodes, each associated with a corresponding input electrode.

17. The apparatus recited in claim 15, further comprising a programmable timer coupled to a power switch in said portable means, said timer disconnecting a power source through said power switch to the remainder of said portable means when the currents from all the electrode pairs have been measured.

18. The apparatus recited in claim 9, wherein said means for comparing, said second means and said means for assessing comprises a computer having appropriate software.

19. The apparatus recited in claim 18, further comprising a point-search electrode which allows the user to determine an appropriate location for disposition of a site-specific electrode and means for monitoring the electrical current value from said point-search electrode whereby the user can select the location of the site-specific electrode providing the highest value.

20. The apparatus recited in claim 18, further comprising a tracer electrode having a rotatable conductive element which allows the user to determine an appropriate location for disposition of a site-specific electrode and means for monitoring the electrical current value from said point-search electrode whereby the user can select the location of the site-specific electrode providing the highest value.

21. The apparatus recited in claim 18, further comprising a vibro-pulse generator for providing pulses to massaging electrodes coupled to the organism to provide a massaging effect.

22. The apparatus recited in claim 18, further comprising an EKG device coupled to said computer.

23. The apparatus recited in claim 2, further comprising a display device coupled to said computer for displaying measured results, displaying messages and displaying the bioenergygram.

24. The apparatus recited in claim 2, further comprising means for sensing said electrical current from a particular electrode pair for a predetermined time, and means for accepting the highest value sensed during said predetermined time as the measured value.

25. The apparatus recited in claim 24, further comprising means for accepting the highest value comprising a switch button depressible when the highest value has been sensed.

26. The apparatus recited in claim 25, further comprising means for sampling said electrical currents generated by an electrode pair as a series of samples, and means for accepting the highest reading in a defined number of samples prior to depressing said switch button.

27. The apparatus recited in claim 24, further comprising means for automatically determining the highest value sensed during the predetermined time as the measured value.

28. The apparatus recited in claim 27, further comprising means for automatically stepping through all electrode pairs in a defined sequence to obtain said current measurement.

29. The apparatus recited in claim 28, further comprising means for rejecting a measurement if the measurement is outside a prescribed range.

30. The apparatus recited in claim 29, further comprising means for rejecting a current measurement if it is substantially zero, reflecting a lack of contact between a particular electrode and the organism.

31. The apparatus recited in claim 30, further comprising means for providing a message to a user to check a corresponding electrode if the current measurement from that electrode pair is substantially zero.

32. The apparatus recited in claim 2, further comprising means for generating a prescription based on the assessment of the physical condition of the organism.

33. The apparatus recited in claim 2, wherein said site-specific and common electrodes comprise polarizable material.

34. The apparatus recited in claim 33, wherein the electrodes comprise Cu, Zn, Ag or AgCl.

35. The apparatus recited in claim 2, wherein said site-specific electrodes are non-polarizable and said common electrode is polarizable.

36. The apparatus recited in claim 35, wherein the non-polarizable electrodes comprise C.

37. The apparatus recited in claim 2, wherein said first means comprises:
    an input demultiplexer for sampling the currents from each of said electrode pairs;
    a resistance coupled to the demultiplexer for passing the current from each electrode pair and converting the current to a voltage drop; and
    an analog to digital converter for measuring the voltage across the resistance corresponding to each electrode pair and converting the voltage to a digital signal.

38. The apparatus recited in claim 37, further comprising an output demultiplexer for converting the output of the analog to digital converter in parallel format to serial format.

39. The apparatus recited in claim 38, further comprising control means for controlling said input demultiplexer, analog to digital converter and output demultiplexer.

40. The apparatus recited in claim 39, further comprising a power supply for supplying power to said apparatus.

41. The apparatus recited in claim 40, further comprising isolation means for preventing the possibility of user shock, said isolation means coupling said power supply and the remainder of said apparatus.

42. The apparatus recited in claim 41, wherein said isolation means comprises an isolation transformer.

43. The apparatus recited in claim 38, further comprising a computer coupled to said control means.

44. The apparatus recited in claim 43, further comprising isolation means coupling said computer and said first means and said control means.

45. The apparatus recited in claim 44, wherein said isolation means comprises optical coupling means.

46. The apparatus recited in claim 2, further comprising a resistance and measuring device electrically unconnected to the remainder of said apparatus for allowing a user to measure currents from the respective electrode pairs.

47. The apparatus recited in claim 2, wherein said common electrode comprises a plurality of common electrodes, each associated with a corresponding input electrode.

48. The apparatus recited in claim 1, further comprising means for developing therapy for the organism dependent on said assessment of the physical condition of the organism.

49. The apparatus recited in claim 1, wherein said value for each electrode pair is a component of an average value for all electrode pairs.

50. The apparatus recited in claim 1, further comprising means for sensing the temperature of the organism at least at one point and means for correlating said sensed temperature to at least one of the current measurements.

* * * * *